United States Patent [19]

Fuller

[11] 3,949,388
[45] Apr. 6, 1976

[54] PHYSIOLOGICAL SENSOR AND TRANSMITTER

[75] Inventor: Charles H. Fuller, Carson, Calif.

[73] Assignee: Monitron Industries, Inc., Santa Ana, Calif.

[22] Filed: Mar. 26, 1975

[21] Appl. No.: 562,083

Related U.S. Application Data

[63] Continuation of Ser. No. 306,097, Nov. 13, 1972, abandoned, which is a continuation-in-part of Ser. No. 199,847, Nov. 18, 1971, abandoned, and a continuation-in-part of Ser. No. 199,979, Nov. 18, 1971, abandoned, and a continuation-in-part of Ser. No. 199,675, Nov. 17, 1971, abandoned.

[52] U.S. Cl. .......................... 340/189 M; 128/2.1 A
[51] Int. Cl.² ............................................ G08C 19/26
[58] Field of Search .............. 340/189 M; 128/2.1 A

[56] References Cited
UNITED STATES PATENTS

3,034,356   5/1962   Bieganski ........................ 340/189 M

*Primary Examiner*—Thomas B. Habecker
*Attorney, Agent, or Firm*—Jones, Tullar & Cooper

[57] ABSTRACT

A small self-contained sensor and transmitter assembly including a sensor for detecting physiological and bio-medical phenomena and a transmitter for transferring such data to a receiver for display and other use is disclosed. In one embodiment, the sensor is adapted to be secured within the axilla of a patient to detect his temperature by means of a thermistor arranged in heat exchange relation with the body of the patient. The thermistor modulates the pulsing rate of a blocking oscillator which generates a magnetic field, the pulsing rate being proportional to the physiological phenomenon of interest. The oscillator, power supply, antenna, and other circuit elements are mounted within corresponding compartments in a molded plastic housing, the arrangement being such that substantially all of the interconnections between circuit elements are made using only the component lead wires. The thermistor is mounted on the exterior surface of the housing and is thermally isolated from it to provide a fast response, and an adhesive is provided to secure the housing to the patient's skin. A resilient cover on the housing provides thermal insulation and insures patient comfort. The transmitter circuitry is constructed for stable operation, fast response, and transmits data in a narrow frequency spectrum for accurate measurement.

57 Claims, 19 Drawing Figures

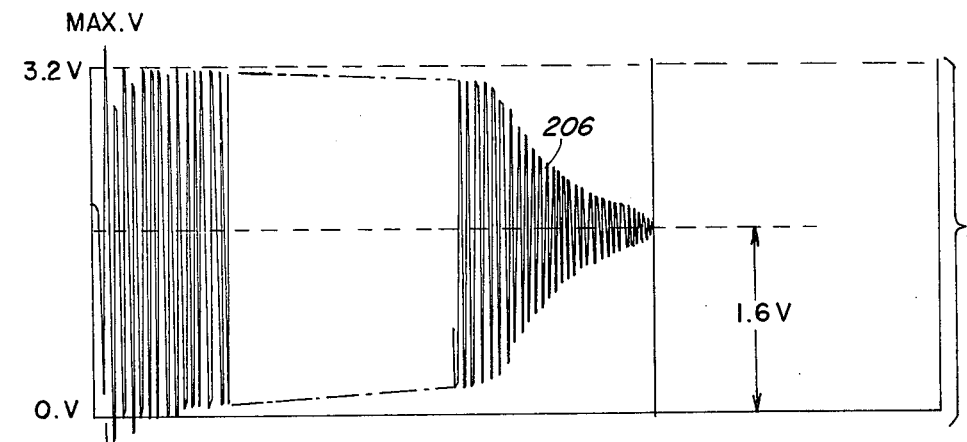
FIG.10A
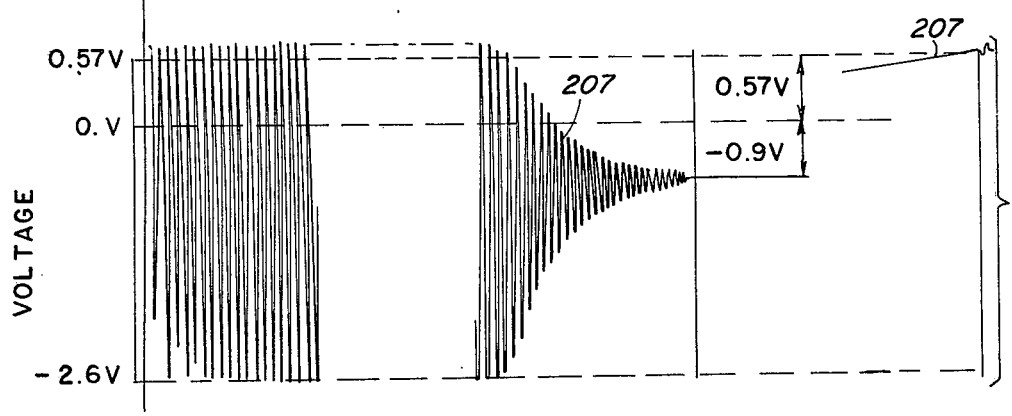
FIG.10B
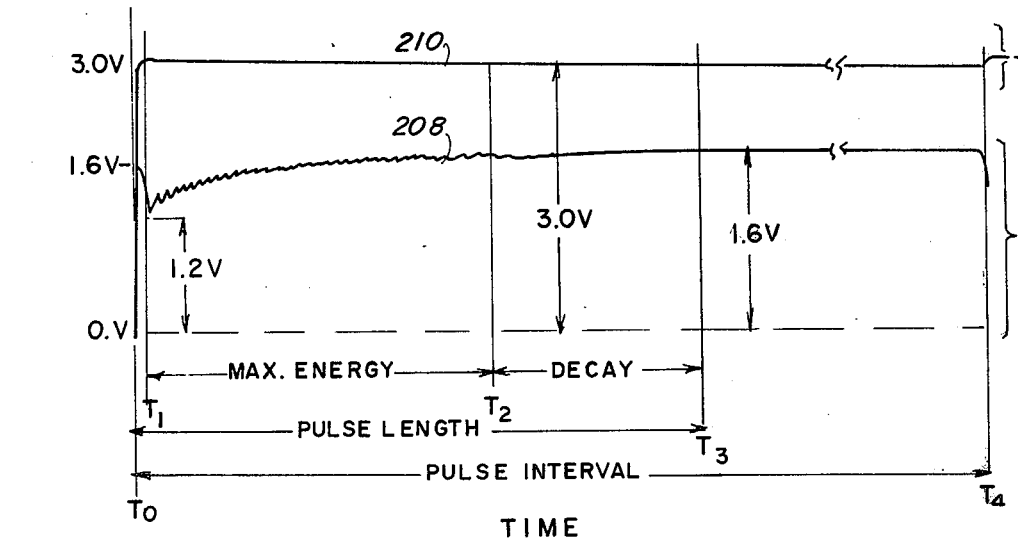
FIG.10C
FIG.10D

PHYSIOLOGICAL SENSOR AND TRANSMITTER

This application is a continuation of application Ser. No. 306,097 filed Nov. 13, 1972, now abandoned, which is a continuation-in-part of copending application Serial No. 199,847 of Charles H. Fuller, filed November 18, 1971, for a "Physiological Transmitter," of copending application Serial No. 199,979 of Charles H. Fuller, filed November 18, 1971 and entitled "Bio-Medical Transmitter," and of copending application Serial No. 199,675, of Charles H. Fuller, filed November 17, 1971, for a "Physiological Testing System" all of which are now abandoned. This application is also related to a copending application Serial No. 200,368 of Carl E. Herring, filed November 19, 1971, for a "Measuring and Display System," now abandoned, and to a copending application Ser. No. 306,253 of Charles H. Fuller and Carl E. Herring, filed Nov. 13, 1972 for a "Physiological Measurement Display System." All of these applications are assigned to the assignee of the present application.

BACKGROUND OF THE INVENTION

The present invention relates, in general, to the field of bio-medical telemetry, and more particularly to a sensor-transmitter for use with human patients under clinical or ambulatory observation.

The detection and measurement of physiological data has become a highly developed art in recent years, and many systems have been designed for this purpose. Such systems have included sensors of various types which may be secured to a patient to detect various phenomena and which produce electrical signals carried by means of electrical leads to suitable measuring and displaying equipment. However, for many purposes, the requirement for a cable connection between a measuring device and a sensor is undesirable, for it not only is uncomfortable to the patient, but it substantially restricts his freedom of movement. Accordingly, telemetry systems utilizing a small, self-contained transmitter in combination with the sensor have been used to transmit the sensed data to a remote receiver. Such systems are described, for example at pages 148 to 160 of "Bio-Medical Telemetry," by R. Stewart MacKay, (Second Edition, Wiley, 1968). Typically, the transmitters of such systems utilize a suitable blocking oscillator having a resonant circuit, the winding of which serves the dual function of tuning the oscillator and generating a radio frequency field which may be detected by the antenna of a receiver. The oscillator is modulated by the sensor to emit bursts or pulses of radio frequency energy at a rate that corresponds to the magnitude of the parameter being measured.

Sensor-transmitters of this general type are very advantageous were remote measurements of parameters are required or desirable. However, numerous difficulties have been encountered in the past in the use of such transmitters, for they have often been inaccurate, unreliable in operation, and difficult to manufacture. One common difficulty resides in the fact that the antenna winding used to transmit the radio frequency, and thus the resonant circuit of which it is a part, may be loaded electrically by an external object, which loading may vary from time to time in accordance with the nature and location of the external object. Such loading affects the burst rate of the transmitter oscillator, so that the output does not always bear a fixed relation to the magnitude of the phenomenon under investigation, but will depend in a variable manner upon the presence and nature of such external objects. Such a system can produce erroneous, or at least unreliable or misleading, indications of the phenomenon under investigation. This is particularly a serious problem where physiological data is being monitored, for human tissue can produce such a loading effect, and this can result in an erroneous reading of, for example, the temperature of a patient undergoing medical observation, if the device has not been carefully calibrated to take into consideration the loading effect created when the transmitter is secured to the skin of the patient.

Additional problems are encountered in the use of prior sensor-transmitters in that such devices are generally susceptible to considerable interference in the radio-frequency bands, making it difficult to obtain accurate readings over a short period of time without resorting to complex coding systems and the like. An additional problem in such devices has been that of obtaining a fast response to a temperature measurement, while preserving the stability of operation of the device and maintaining an accurate measure of the parameter of interest. Since small self-contained transmitters of this type are generally battery-powered, another problem that has been encountered is the provision of a circuit that will produce a reliable output over the period of life of the battery.

In the prior copending applications, referenced above, a small, self-contained physiological transmitter assembly has been described which overcomes many of the difficulties of prior art systems; however, the device of those applications was designed for a one time use, for the battery power supply was built as an integral part of the device. Although it has now been found that a single-use device of this type is not sufficiently economical, the requirements for accuracy of measurement in a mass-produced item could not be met in any other way at the time of that application.

One of the prime requirements for a sensor-transmitter of this type is that it be small and light in weight, so that it will be comfortable and safe to wear. This requires a very compact circuit arrangement and in order to insure that the frequency of operation of the device remains within a predetermined range and that each sensor-transmitter produces the same output characteristics, the arrangement of elements within the housing becomes critical to an accurate measurement of the parameter being monitored. Further, the placement of elements must be easily reproducible, so that the unit can be mass-produced while still obtaining identical data from each one with a minimum of calibration. In addition, to reduce the cost of the unit, the circuit arrangement must be such that it may easily be assembled and can be adapted for automated assembly. Further, care must be taken to insure that the transmitted signal itself does not interfere with the sensor, and thus affect the accuracy of the device.

SUMMARY OF THE INVENTION

Accordingly, it is an object of the present invention to produce a reliable and accurate device for sensing data to be measured and transmitting signals corresponding to such data accurately and reliably.

It is another object of the present invention to provide a small, self-contained physiological sensor and transmitter assembly which may be removably secured to a patient and which will be comfortable to wear, safe, and easy to use.

It is another object of the invention to provide a transmitter of bio-medical data which correctly and reliably presents the phenomenon under investigation independently of any loading to which the transmitter may be subjected by external objects.

Another object of the invention is to provide a transmitter in which the emitted signals are concentrated within a relatively narrow frequency band whereby the transmitter requires lower power and thus has a longer life than prior devices for a given transmitter's data transmission distance.

It is another object of the invention to provide a sensor-transmitter assembly which is accurate, reliable, and provides a high degree of stability and a fast response, to measured parameters at a low cost and under a variety of conditions.

Another object of the invention is to provide a sensor-transmitter unit which is highly reproducable and in which the critical arrangement of elements is assured, whereby a compact, low-cost unit having a high degree of accuracy is produced.

In accordance with the present invention, a small, self-contained physiological sensor and transmitter assembly is provided in a small housing which may be removably secured to a patient. In the simplest form of the invention, a double-faced adhesive sheet is secured to one side of the housing to facilitate placement of the unit on the skin of the patient, while the other side of the housing is covered with a pliant material to render the device comfortable to wear within the axilla or elsewhere.

The housing for the transmitter-sensor is constructed of a molded plastic, and is formed to provide a chamber for each component of the transmitter circuitry to assure that the various elements are correctly arranged for proper operation. Each element has a specific location with the arrangement being such that the normal component leads or, as in the case of integrated circuit chips, the conductive termination may be used to provide the required interconnection between the elements. For speed and reliability, each lead is cut to length, bent to its appropriate connection point, and the leads are connected together by means of a quick setting, electrically conductive epoxy.

To provide compactness, and reduce RF power absorption, the battery supply for the unit is located within the antenna winding and is accessible by way of an opening in the housing to permit battery replacement. The leads to which the sensor is connected extend through appropriate openings in the housing, so that the sensor device may be secured to the exterior of the housing and connected to the appropriate leads. The sensor is mounted on a glass microsphere filled epoxy which thermally insulate the sensor from the housing.

Also extending through openings in the housing are a pair of switch leads which are mechanically separated to hold the circuit in an inoperative condition to assure a long shelf-life for the unit. A switch cover is provided to mechanically interconnect the switch leads to activate the device, the switch cover snapping into place to provide a substantially permanent activation of the unit.

In a preferred embodiment, the transmitter comprises a blocking oscillator which is capable of producing bursts of radio frequency energy, with the bursts being repetitive at a rate determined by the sensor unit.

In a preferred embodiment, this sensor is a thermistor adapted to measure the temperature of a patient, although other forms of sensor may be used equally well. These bursts of radio frequency (RF) energy are generated in a resonant tank circuit which includes an inductor, the windings of the inductor also act as the antenna for the transmitter device. However, it will be understood that the RF signals generated by the transmitter of the present device are not intended to be detected by a receiver located a long distance away from the sending unit; the present device is designed for use in the "near-field" region of the transmitter. The near-field region, generally considered to be located within approximately seven wave lengths of the transmitter antenna, utilizes the inductive effects of the alternating field generated by the transmitter. Near-field effects are discussed briefly in "Radio Engineers Handbook" by F. E. Terman (McGraw-Hill, 1943), and are characterized by a different fall-off rate and by a different relation between the alternating magnetic and electrical components of the field than is the case in the more conventional RF "far-field" region. Thus, for example, the far-field electrical and magnetic field strengths are proportional to each other, and the amplitude of each falls off inversely with the distance; on the other hand, an induction field, the near-field intensity falls off inversely with a power of distance; for example, as the square or the cube of distance.

Since the system of the present invention is particularly useful in the extreme near-field region of the transmitter, the relationship between the transmitter and the receiver is in the nature of a loosely coupled transformer, with the primary winding being the antenna of the transmitter and the secondary winding being the antenna of the receiver. In the transmitter, the antenna takes the form of a winding that encircles a ferromagnetic core in the shape of a hollow cylinder with open ends, while the receiver employs an antenna in the form of a secondary winding of similar construction. With such a transformer, the strength of the induced field falls off at a much more rapid rate than is the case with either the "far-field" or the "near-field" ordinarily utilized in a radio transmission. Although such a characteristic is not usually desirable in a wireless communication system, it is desirable for bio-medical purposes, where a condition of a patient must be observed with great accuracy and reliability, without interference from nearby sources of radio frequency energy. Thus, the parameter-sensing transmitter element is mounted in direct contact with the patient, while the receiver is located within a few feet of the transmitter; that is, within a distance which is only a small fraction of a wavelength, to take advantage of the characteristics of the inductive field and to avoid interference from nearby transmitters. In a test of field intensity within about 40 inches of the transmitter of the present invention, it was found that the field strength experienced a fall-off rate corrresponding to the inverse power of about 2.75 of the distance from the transmitter.

Although the transmitter in its preferred mode is particularly suitable for use in the extreme "near-field" transformer action region, in some of its forms it is useful in other regions. However, in order to prevent interference between transmitters that may be used, for example, for patients in adjacent beds in a hospital ward, it is preferred that a low power continuously sending transmitter be used.

BRIEF DESCRIPTION OF THE DRAWINGS

The foregoing and additional objects, features and advantages of the invention will become evident to those skilled in the art upon a reading of the following detailed description of the invention, taken in conjunction with the accompanying drawings, in which:

FIGS. 10A–10D are graphical illustrations of the waveform in the transmitter of FIG. 9;

DETAILED DESCRIPTION OF A PREFERRED EMBODIMENT

Figure 1:
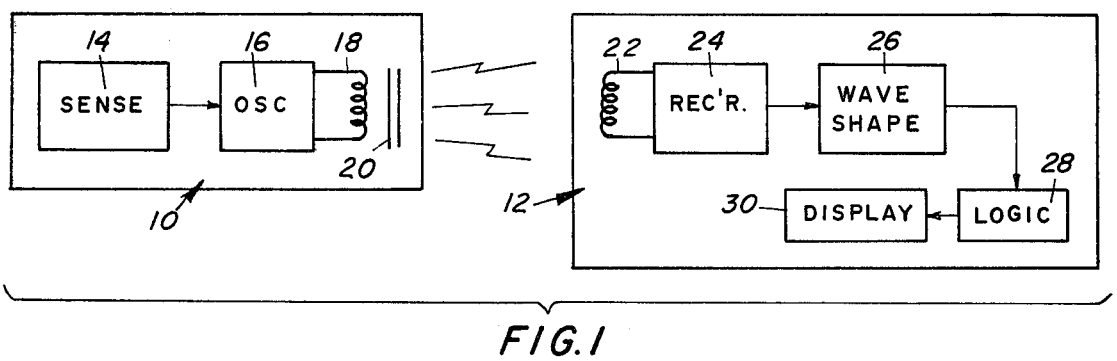
FIG. 1 is a block diagram of a transmitter and receiver system embodying the present invention.

Turning now to a consideration of the present invention, there is illustrated in FIG. 1 a telemetering system embodying the present invention. For purposes of illustration, the invention is described herein in terms of a temperature sensor for use in monitoring over a substantial period of time the temperature of, for example, a hospital patient. For convenience, the system may thus be referred to as a telethermometer transmitter assembly 10 and an associated telethermometer receiver assembly 12. The transmitter assembly 10 includes a sensor 14, such as a thermistor or other temperature-variable component, producing an output that serves to modulate a carrier wave generator such as a blocking oscillator 16. The oscillator output appears on an output winding 18 which is wound on a ferro-magnetic core 20 and serves as an antenna for the sender unit 10. The transmitter oscillator generates an alternating magnetic field that varies at radio frequency, this RF output being pulse modulated at a burst rate corresponding to the temperature or other parameter to which the sensing element 14 is exposed.

The transmitter unit 10 is of very low power, being driven in the preferred embodiment by a single energy cell which, when activated, will provide an operating life of at least two weeks. Over this period of operation, the transmitter will continuously produce bursts of RF energy at a burst rate corresponding to the measured temperature and with an accuracy that will meet applicable requirements for oral mercury thermometers. These pulses, or bursts, each have, for example, a length of 15.2 microseconds, with the RF carrier frequency of the pulse having its spectrum centered at 4.2 megaHertz (mHz). In a preferred embodiment, the pulse rate is set at 1831 pulses per second (pps) at sensor temperature of 101° F., with the characteristic pulse rate versus temperature characteristic of the unit having positive slope of approximately 48.2 pps per degree F. Only the pulse rate varies with temperature, the remaining operational characteristics of the sender unit remaining stable. The battery current drain at this pulse rate is approximately 32.1 microamperes, enabling the device to operate continually for about two weeks without varying from the required pulse rate tolerances.

The transmitter assembly is packaged in a housing which requires a volume of less than ¼ cubic inch and is enclosed in a soft cellular urethane cover on one side and an adhesive pad on the other to permit attachment of the device. The unit is easy to assemble and calibrate, attains a fast rate of thermal response, and maintains the required accuracy.

The transmitter and receiver units are entirely separate, with the sender preferably being attached to a patient and the receiver being hand-portable for use by medical personnel in measuring the temperature of a patient. The receiver is a hand-held remote digital indicator which is battery powered and is sufficiently selective in its response to enable the operator to obtain an accurate reading from only the closest sensor transmitter, and is not susceptible to interference from the ordinary hospital noise environment. Although the preferred range of response to a transmitter is less than three feet, accurate readings can be obtained at a greater distance and, where other sensors are not interfering, the receiver is capable of providing accurate readings seven feet or more away from the transmitter. The receiver responds in less than one second to the operation of its monitoring switch to display a reading of temperature, and will maintain this reading until the button is released.

The telethermometer receiver unit 12 incorporates a loop antenna 22 which intercepts the signals transmitted by the sender unit 10 and feeds them through a receiver 24 and a wave shaper 26 to convert them into square wave signals at the audio frequency of the pulse modulation. The output of the wave shaper is fed to logic circuitry 28 which includes a clock circuit generating pulses at a fixed frequency. The logic circuitry gates the clock circuit for a precise period of time corresponding to the pulse rate of the received signal, thereby producing a number of pulses that exactly corresponds to the measured temperature. A counter circuit responds to this pulse train and converts it to a readout signal which displays on a display unit 30 or other indication that varies with the received burst repetition rate. This display unit may be calibrated in any way desired, but in the preferred embodiment disclosed herein, it is calibrated to display in degrees Fahrenheit the temperature detected by the sensing element 14. A receiving unit suitable for use with the transmitter disclosed herein is described in copending application Ser. No. 199,675 of Charles H. Fuller and copending application Ser. No. 200,368 of Carl E. Herring, noted above. An improved receiving unit also suitable for use with the transmitter of the present invention is disclosed and claimed in application Ser. No. 306,253 of Charles H. Fuller, filed on even date herewith, and entitled "Physiological Measurement Display System."

Figure 2:
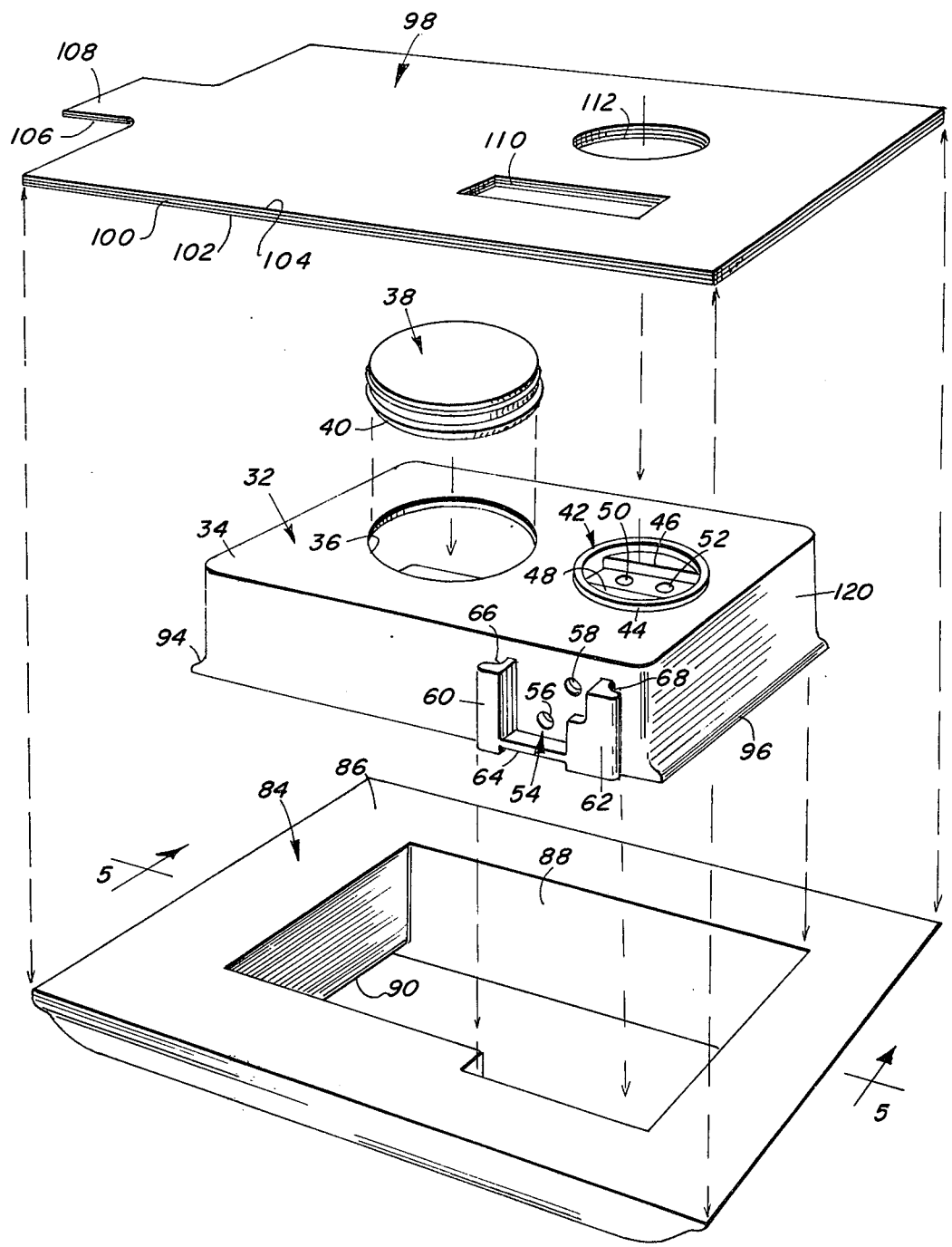
FIG. 2 is an exploded perspective of one embodiment of the housing for the transmitter of the present invention.

The housing in which the transmitter unit of the present invention is located is generally indicated at 32 in FIG. 2. The housing is in the form of a generally rectangular case which, in a preferred embodiment, is 1 inch long and 0.6 inch wide and 0.25 inch deep. The casing is injection molded of a suitable plastic material, such as filled polyester plastic which is capable of high precision molding and is strong enough to give the device a high degree of dimensional stability so as to protect the electrical components which it carries. As shown in the exploded perspective view of FIG. 2, the bottom surface 34 of the housing is formed with an opening 36 through which the battery which powers the transmitter may be inserted or removed. A cover 38 of a high strength plastic material such as that sold by the General Electric Company under the name LEXAN, is provided for the opening 36. The cover is provided with a peripheral rim, or flange, 40 which snaps into and engages the sides of opening 36 to hold the power supply battery in the housing and to provide a tight seal for the opening.

Also formed on the bottom of casing 32 is a sensor element receptacle 42 which is designed to receive a sensor, or transducer, for monitoring a desired physiological parameter. The transducer may be, for example, a thermistor for use in measuring the temperature of a patient, but other transducer elements may be used. The receptacle is surrounded by an upstanding annular rim 44 and may include two ledges, or shoulders, 46 and 48 for receiving and supporting the sensor element. A pair of apertures 50 and 52 are provided in the bottom of the receptacle and lead to the interior of the casing to accomodate electrical leads from the transmitter circuit.

Figure 3:
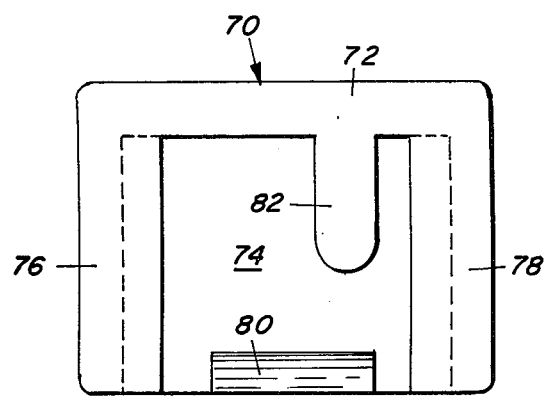
FIG. 3 is an elevation view of a switch cover for use with the transmitter housing of FIG. 2.
Figure 4:
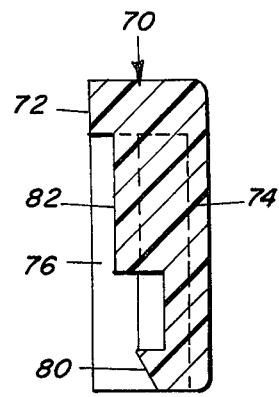
FIG. 4 is a sectional view taken along lines 4—4 of FIG. 3.

On one side of the casing is formed a switch cavity 54 into which component leads from the transmitter circuitry are led by way of apertures 56 and 58. The cavity is defined by a pair of sidewalls 60 and 62, and a bottom wall 64. The sidewalls are grooved as at 66 and 68 to receive a switch cover 70 such as that illustrated in FIGS. 3 and 4. The switch cover, as viewed from the back in FIG. 3 and in section in FIG. 4, is generally in the form of an inverted L, with one leg forming a top portion 72 and the other leg forming a front portion 74, the leg 72 being adapted to span the tops of the sidewalls 60 and 72 and the front portion being adapted to span the sides thereof to complete the enclosure of switch cavity 54. The cover is held in place by means of side flange portions 76 and 78, which are adapted to enclose the sidewalls 60 and 62, with the ends of the flanges extending into grooves 66 and 68 to securely hold the cover in place. Formed at the bottom edge of the front wall portion 74 is a shoulder portion 80, which is designed to engage the lower surface of bottom wall 64 when the cover is in place. The shoulder portion snaps into place under the bottom wall when the cover is pressed downwardly, the snap action holding the cover firmly in place, so that it cannot easily be removed.

A depending tongue 82 is formed on the inner surface of wall 74 of the switch cover, the tongue 82 serving to press together switch wires extending into the switch cavity through apertures 56 and 58 to activate the transmitter. The snap action of the cover prevents its removal, so that the transmitter will remain in operation, after once being activated, until the battery supply has been depleted. The unit may then be returned to the supplier for removal of the switch cover, replacement of the battery and, if necessary, recalibration.

Figure 5:
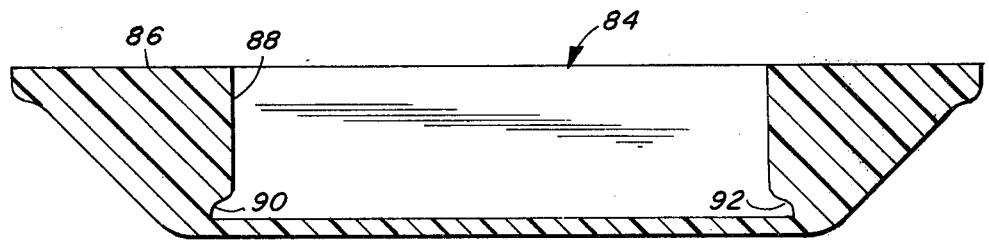
FIG. 5 is a sectional view of the housing cover, taken along line 5—5 of FIG. 2.

The exploded view of FIG. 2 illustrates at 84 the soft flexible cover that is used to enclose and protect the sides and top of the casing 32, so that the unit will be comfortable for the patient to wear. As shown in FIG. 2, and in the sectional view of FIG. 5, the cover is formed with a flat bottom surface 86 and a centrally located cavity 88 which is shaped to receive the casing 32, the cavity being sufficiently deep that when the casing is in place the flat bottom surface 86 will be flush with the bottom surface 34 of the casing. The cavity is formed with a pair of outwardly extending grooves 90 and 92 which are adapted to receive corresponding flanges 94 and 96 formed on the end walls of the casing. The flexibility of the cover allows the casing to be snapped into and securely held in the cavity 88 and its flexibility and resiliency makes the assembly comfortable for the wearer of the sensor-transmitter when it is mounted in the axilla or the like. As shown in FIG. 5, the cover is molded with smooth rounded corners and with sloping edges to provide maximum comfort.

Besides providing comfort and protecting the electrical components within the casing, the combination of the cover and the casing provides thermal insulation of the electrical elements on the side remote from the wearer's skin, thus reducing heat exchange with the atmosphere or with an object such as the patient's arm, which might contact the cover. This insulation insures that the transmitter will remain stable in its operation even when the sensor-transmitter unit is alternately covered and exposed to room temperature, as when the patient lowers or raises his arm. The cover may be molded from a soft vinyl plastic, if desired, but to provide a greater degree of thermal insulation it is preferred that a closed cell urethane plastic be used.

To secure the sensor unit in place, a double-faced adhesive pad 98 is provided. This pad comprises a central layer 100 which is coated on both sides with an adhesive. This adhesive coating is then covered on one side by a removable waxed paper cover 104. Suitable tabs 106 and 108 are provided on the ends of layers 100 and 104, the tabs 106 and 108 facilitating removal of the paper layers to expose the adhesive coatings. The adhesive pad includes a rectangular opening 110 which is adapted to be aligned and to accomodate the switch cover 70, whereby the switch can be operated when the pad is in place, and a circular opening 112, which is adapted to be aligned over the sensing element of the sensor-transmitter unit.

The double-faced adhesive pad is of the type which has been approved for medical purposes, and may be, for example, No. 1522 Brand double-coated medical tape, manufactured by 3-M, Inc. Such a tape has a polyethylene backing and employs a synthetic acrylic copolymer adhesive.

The transmitter unit is assembled, after completion of the interior electrical circuitry to be described, by snapping the casing 32 into the vinyl cover 84, removing the paper layer 102 from the adhesive pad, and attaching the pad by means of the exposed adhesive coating to the bottom surfaces 34 and 86 of the housing and cover, respectively. This secures cover 84 on the casing 32 and provides a small, easily handled sensor unit.

In use, the switch cover 70 is pressed into position through opening 110 of the adhesive pad to activate the transmitter unit. The paper layer 104 is then stripped from the adhesive layer 100, thereby exposing an adhesive surface by means of which the transmitter unit may be secured to the skin of the patient, for example, in the area of the axilla, with the sensing element extending through opening 112 and firmly contacting the patient's skin. Once activated, the transmitter will continue to operate, transmitting pulsed signals corresponding to the sensed temperature in the manner to be described, until the battery charge is dissipated, a period of about 2 weeks under normal conditions. The non-reversible snap action of the power switch assures proper continuous action for this period of time.

Figure 6:
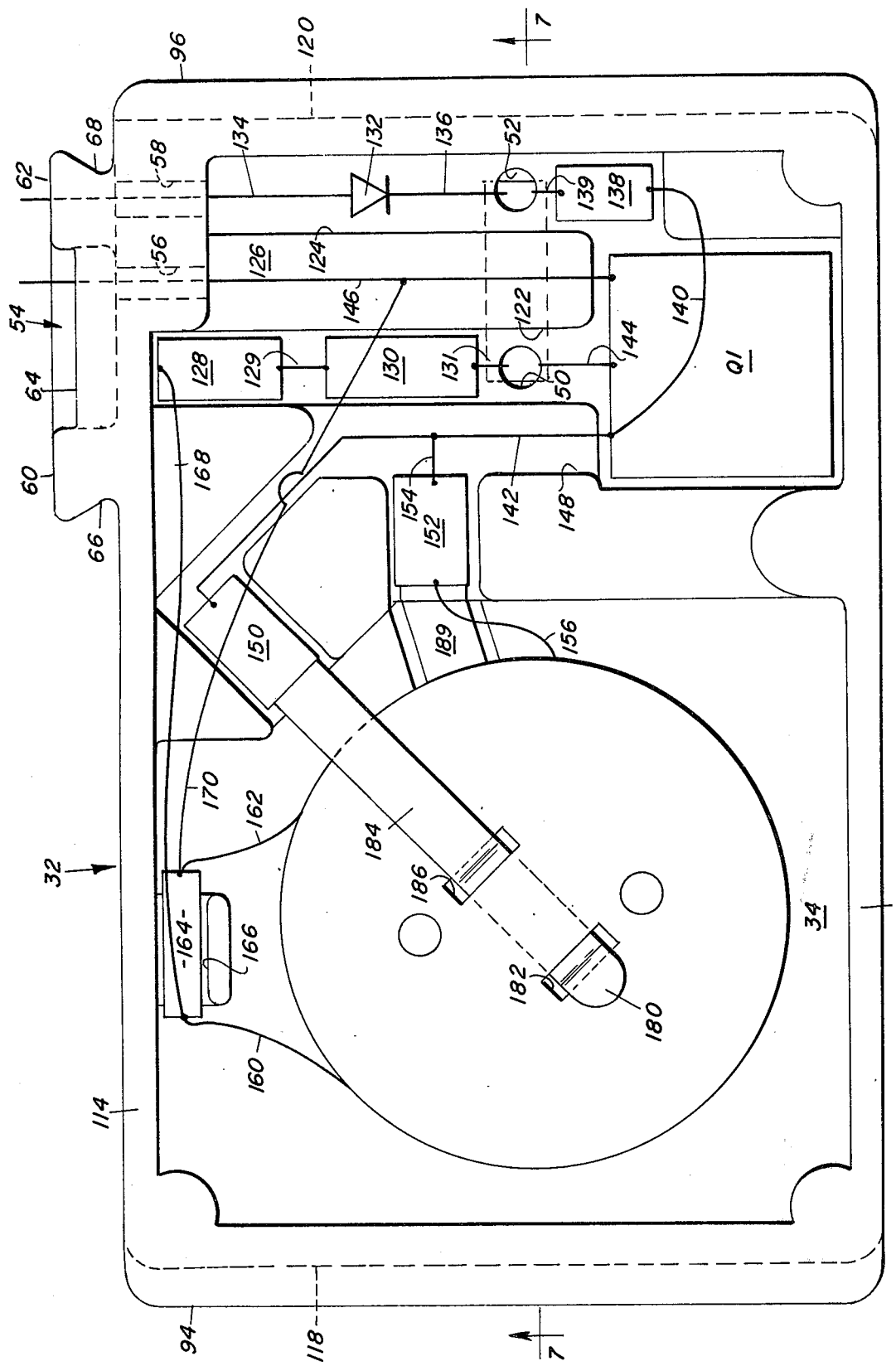
FIG. 6 is a bottom plan view of the housing of FIG. 2 with the cover removed, showing the arrangement of electrical components therein.
Figure 7:
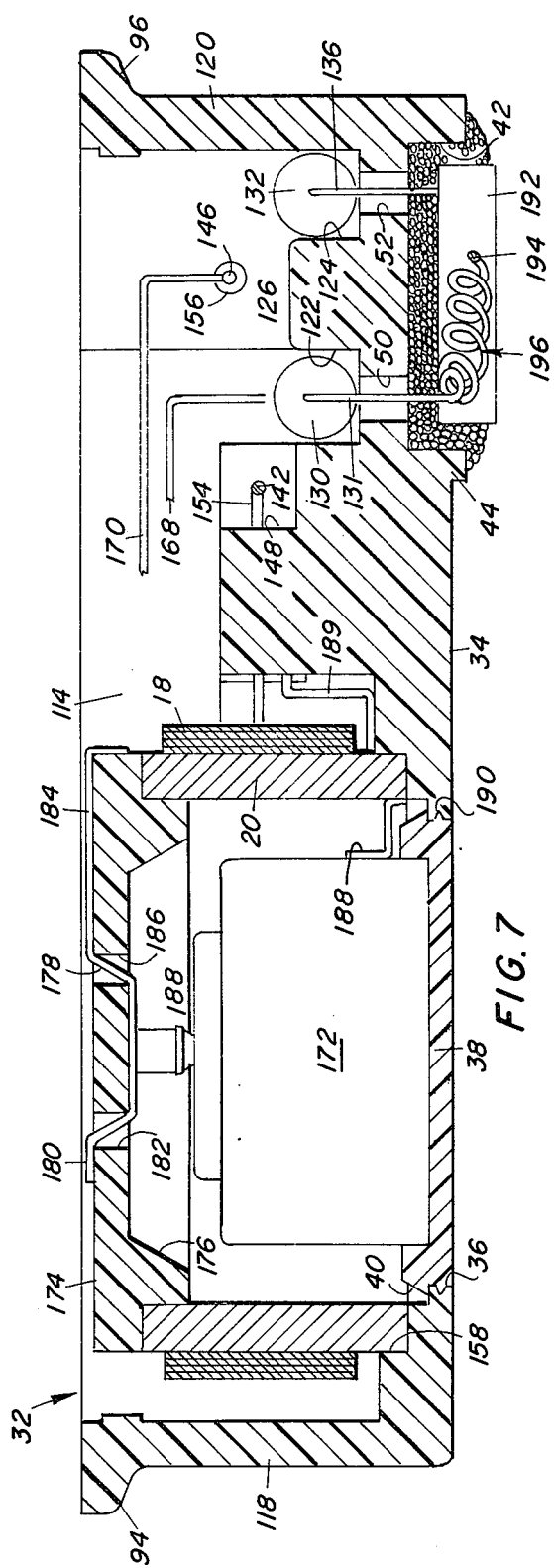
FIG. 7 is a sectional view taken along line 7—7 of FIG. 6.

Turning now to FIGS. 6 and 7, it will be seen that the interior of housing 32 is formed in such a way as to receive and properly locate the various circuit components which make up the transmitter. Thus, the casing is shown to be made up of a bottom wall 34, front and back walls 114 and 116, and end walls 118 and 120.

As may be seen in FIG. 6 a pair of transversely extending parallel grooves, or depressions, 122 and 124, are provided in the bottom of the housing, the grooves being separated by a ridge 126. Groove 122 is adapted to receive a capacitive element 126 and a resistive element 130 arranged end-to-end, with one lead of resistor 130 being connected to a corresponding lead on 128 and the other lead of resistor 130 extending through aperture 50 in the casing into the sensor element receptacle 42. A diode element 132 is positioned in groove 124, with one lead 134 extending through aperture 158 into the switch cavity 54 and the other lead 136 extending through aperture 52 into the sensor receptacle. Also located in groove 124 is a capacitive resistive element 138 having one lead connected to lead 136 of the diode and extending through aperture 52, and the other lead 140 connected to the emitter lead 142 of a transistor Q1. The transistor is located in a cavity formed in housing 132 to receive it, the cavity being adjacent the back wall 166 and at the ends of grooves 122 and 124.

The base lead 144 of transistor Q1 is connected to lead 131 of resistor 130, and extends through aperture 50 into the sensor receptacle, while the collector lead extends from Q1 along the top of ridge 126 and through aperture 56 to the switch cavity 54. Adjacent groove 122, and to the left thereof as viewed in FIGS. 6 and 7 is a lesser depression or groove 148, which is aligned with and adpted to receive the emitter lead 142 of Q1 and which angles away from groove 122 to accomodate the lead from a resistive element 150 to which the emitter lead is connected. A capacitive element 152 is located in a branch of depression 148 and has one of its leads 154 connected to emitter lead 142. The other lead 156 of capacitor 152 is connected to a tap on the antenna winding 18, which is wound on coil form 20.

The antenna winding core 20 is mounted in cavity 158 (FIG. 7) formed on the bottom wall of the casing and surrounding aperture 36, the cavity 158 holding the core securely in place. Two additional taps 160 and 162 lead from the antenna winding to opposite ends of a capacitor 164, secured in a channel 166 formed against the front wall 114 of the casing. One of the leads 168 of capacitor 164 is secured to capacitor 128, while the other lead 170 of capacitor 164 is secured to the collector lead 146.

In order to conserve space within the sensor-transmitter casing 32, a power supply battery 172, which preferably is a single cell, but which may comprise a plurality of cells, is mounted within the annular core member 20, the battery receptacle being defined by the core, the battery cover 38, and a cap 174 which closes the upper end of the core as viewed in FIG. 7. This cap is designed with a depending flange portion 176 which extends into and engages the interior surface of core element 20. Mounted in the cap is a battery contact and lead assembly 178 having a first arm 180 which extends upwardly from an aperture 182 in cap 174 and is bent over against the top of the cap to secure the battery contact. Similarly, a second arm 184 extends upwardly through a second aperture 186 and is folded over across the top of the cap. Assembly 178 includes a battery contact element 187, which is spring loaded to maintain a firm contact with the battery. Preferably, the contact 187 is formed by punching a hole partially through a piece of sheet metal, producing sharp edges around the edge of the contact, to assure good electrical connection with the battery terminal. As may be seen in FIG. 6, the battery arm 184 is connected to the remaining lead of resistor 150.

A second spring loaded battery contact is secured to the side of core 20, providing a contact carrying arm 188 extending into the interior of the core element and into contact with the side wall terminal of the battery. The opposite end of the contact extends out of the core 20 to provide a contact arm 189 which may be connected to lead 156 of capacitor 152.

The core 20 is of a suitable ferro magnetic material such as carbonyl iron or the like. Carbonyl iron consists of comminuted iron particles that have been oxydized in a carbonyl atmoshpere, such particles being disbursed in a non-magnetic, non-conductive binder such as epoxy resin. Such a powdered iron core has the characteristics of low eddy current losses and the ability to be easily machined to close dimensional tolerances. Further, the core produces a change in permeability of less than 5 percent after a 400 to 500 Gauss field has been applied and removed and exhibits a retentivity of less than 5 percent.

Prior to machining such an iron core has little or no surface conductivity. During the machining of the iron core to form grooves for the turns of winding 18, for example, the powdered iron particles produced by such machining may introduce a leakage path in the assembly, which may in turn introduce RF losses. This is prevented by treating the core in an acid bath to etch the machined surface and restore its electrically insulative qualities. The powdered material of the tubular core also reduces the effects of loading the winding, reducing the number of turns required and thus the power loss in the winding itself, thereby providing the transmitter with greater range and longer life.

As illustrated in FIG. 7, the closure or battery cover 38 is formed to provide a snap fit into aperture 36, the cover being formed with a peripheral rim 40 to engage the undersurface of the wall-defining aperture 36, as described above, holding the battery in place against the spring loading provided by the contact assembly 178 and thus preventing easy removal of the battery. The closure is also provided with an annular bead 190 which seals the opening 36.

The sensing element, responsive to the physiological parameters to be monitored, is secured to the outside of casing 32 in the sensing element receptacle 42, as illustrated in FIG. 7. Sensing element 192 in this embodiment is a thermistor, or temperature-sensitive resistor, which varies in accordance with the ambient temperature to which it is exposed to produce a corresponding resistance value. The two terminals of the thermistor are connected to the leads extending through apertures 50 and 52, respectively. Thus, for example, the lead wire 144 from the base of transistor Q1 and the lead wire 131 from resistor 130 are connected to one of the terminals 194 of the thermistor. Similarly, the other terminal of the thermistor is connectd to leads 136 and 139. It is preferred that the connection to the thermistor terminals be by means of a bifilar coil of very fine wire, such as that illustrated at 196, the fine wire serving to provide a thermal insulation between the main body of the transmitter and the thermistor. The coil 196 is arranged to be at right angles to the antenna winding 18 so as to minimize radio frequency absorption from the transmitter, the coil having equal numbers of turns in opposite directions so that any induced currents are cancelled. In many applications of the present transmittter, however, the amount of RF energy induced in the thermistor circuit is minimal. In such cases, the use of a bifilar connection is not economically justified and may be omitted.

The thermistor is secured in receptable 42 by an epoxy which is filled with glass microspheres to provide a thermally insulating layer between the thermistor and the casing. Such a layer insulates the casing from the sensing element so that the thermistor is free to respond very rapidly to the temperature of the surface to which it is attached, without being affected by the heat sink provided by casing 32. This almost total thermal insulation of the sensor provides a very fast reaction to temperature changes in the device of the present invention, and allows the circuitry to stabilize long before the components of the system have reached thermal equlibrium with the object to which the casing has been attached.

Although it is not shown, in some embodiments of the invention it may be desirable to electrostatically shield the antenna winding 18 in order to reduce electrostatic radiation to and from the transmitter without substantially reducing the inductive transmission of signals to the receiver winding. Such an electrostatic shield would virtually eliminate the effects of interference from nearby electrostatic fields, and in an industrial application or where there is a heavy radio frequency pulse noise in the area of the system that would affect its operation, the electrostatic shielding would be needed. However, for normal hospital use such shielding is not required, and from a cost standpoint it is uneconomical unless it is absolutely necessary to the operation of the system.

Electrostatic shielding for the antenna may take the form of a thin coating of zinc sprayed onto the outside of winding 18, and on the top of the battery cap 174, as disclosed in copending application Ser. No. 199,979, or Ser. No. 199,847, discussed above. During the spraying of such a shield, a mask is held over a part of the coil to form a break in the coating to prevent the zinc shield from forming a short-circuited secondary winding with the transmitter winding 18. The shield forms an inverted cup-shaped member electrically connected to the upper terminal of the battery by way of battery lead 184 and embracing the battery, the core, and the winding. Alternatively, the shield may be composed of a thin strip of copper surrounding the outside of the winding and having its ends lapped but insulated from each other and electrically connected to the upper terminal of the battery.

To assure proper electrical connections throughout the transmitter assembly, these connections are formed by means of a conductive epoxy cement which drys and hardens at room temperature and provides a secure electrical connection. Thus, in assembling the transmitter, the various component leads are bent into position, cut to length, and secured by a drop of silver epoxy resin. This procedure eliminates the need for soldering and, together with the configuration of the housing which carefully positions all of the circuit elements, permits very accurate and rapid assembly of the unit, without the need for high temperature curing which may shift component values.

Figure 8:
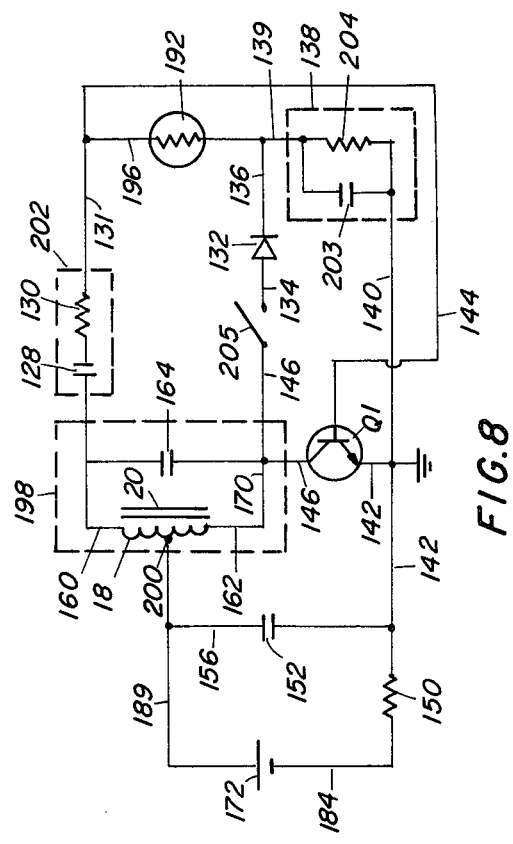
FIG. 8 is a schematic diagram of a preferred form of the transmitter circuitry of the present invention.

The various circuit components illustrated in their mechanical configuration in FIGS. 6 and 7 are shown in the corresponding electrical schematic diagram of FIG. 8, wherein corresponding components are similarly numbered, and to which reference is now made. As connected, the electrical circuit comprises a small, compact blocking oscillator comprising a low voltage transistor Q1, a resonant tank circuit 198, and a feedback circuit including a blocking capacitor 128, powered by a miniature dry cell 172. The tank circuit, which includes the winding 18 and a parallel tuning capacitor 164, is connected at one end to the collector electrode of the transistor. A center tap 200 on the winding 18 is connected through a by-pass capacitor 152 to the emitter electrode 142 of Q1, the capacitor being connected across the battery 172 and a series resistor 150, which forms the power supply for the unit.

The resonant tank circuit 198 is connected between the collector electrode of transistor Q1 and the base thereof by way of a feedback loop which includes an isolating network 202, made up of blocking capacitor 128 and resistor 130, lead line 131, and lead line 144. The base of transistor Q1 is connected by way of line 144, lead line 196, thermistor 192, lead line 139, and RC network 138 to the emitter electrode. The RC network includes a storage capacitor 203 and a resistor 204 connected in parallel between lines 139 and 140. Where the transistor Q1 is of the npn type, the negative terminal of the battery is connected through ballast resistor 150 to the emitter and the positive terminal through the line 189 to the tap 200 in the winding 18. The collector of the transistor is also connected by way of line 146 and a mechanical switch 205 to the anode of diode 132. The cathode of this diode is connected by way of lead line 136 to the junction of thermister 192 with the RC network 138. It will be understood that switch 205 is the circuit equivalent of the switch mechanism formed on the side of the transmitter casing and operated by switch cover 70.

Figure 9:
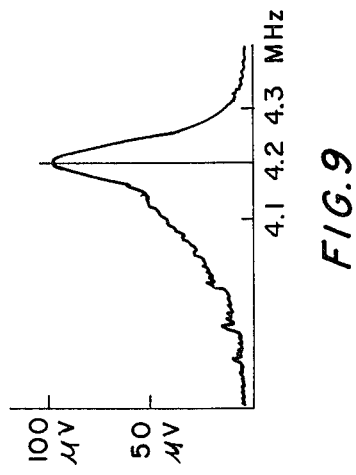
FIG. 9 is a graphical illustration of the radio frequency spectrum of the transmitter.

In the illustrated circuit arrangement, the transistor, the feedback loop, and the resonant tank circuit function as a blocking oscillator, producing recurring bursts of RF frequency signals, the burst, or pulse, rate being controlled by the value of the resistance of thermistor 192. Although modulated blocking oscillators are known, the present circuit is so designed, and the components are so arranged, that a very narrow frequency spectrum is produced during each burst. This frequency spectrum, which is illustrated in FIG. 9, is caused by the fact that the oscillations occurring during a single burst start out at a relatively low value, build up quickly to the nominal value, and then gradually increase until the end of the burst. Thus, there is a wide range of RF frequencies produced during each burst, although in the present circuit approximately 50 percent of the burst energy lies close to the nominal value of the 4.2 mHz, in a frequency band between about 4.15 and 4.25 mHz. The relatively narrow frequency spectrum produced by the present circuit improves the signal to noise ratio of the signal at the receiver and thus improves the range over which adequate reception can be obtained.

In the usual form of a blocking oscillator, no isolating resistor is provided in the feedback loop, and the tank circuit would be connected to the transistor base by way of blocking capacitor 128 only. In that arrangement, when the circuit is initially turned on, a surge of current from the battery flows through the winding 18 and through the capacitor 128 to the base of the transistor, turning the transistor on. The transistor conducts, the collector voltage falls from the battery potential to the ground potential on the emitter, and the tank circuit begins to oscillate. Capacitor 128 slowly discharges, reducing the average base voltage as the circuit oscillates, until the transistor is eventually cut off. The capacitor then charges through the RC circuit 138 and thermistor 192 until the voltage on the base is returned to the trigger value, turning the transistor on and producing another burst of oscillations.

During a given burst, or pulse, the frequency of oscillations may double over the period of the pulse. The reason for this is that the transistor is driven into saturation at the peak of each cycle of the oscillation, and for that period of time the capacitor 128 is essentially connected directly across the winding 18. This changes the LC ratio of the tank circuit and changes its frequency. Since capacitor 128 is gradually discharging during the pulse "on" time, the percentage of a given cycle of oscillation during which there is saturation of the transistor will vary across the width of the pulse, thereby changing the length of time during which the capacitor 128 is effectively in parallel with the tank circuit, and thus producing a gradual change in its LC ratio and a sweep of the effective frequency.

This frequency sweeping is very undesirable in a system of the present type where accurate and rapid measurements are required. Therefore, the present invention utilizes an isolating impedance such as resistor 130 in series with the capacitor 128. This decreases the feedback current between the tank circuit and the base of transistor Q1 and shortens the time that the transistor is saturated during each cycle. Further, the impedance acts to isolate the capacitor 128 from the tank circuit during saturation of the transistor and thus reduces its effect on the LC ratio, thereby reducing frequency drift during the course of a pulse. It will be noted that the insertion of an isolating impedance such as resistor 130 also will slightly increase the pulse rate of the circuit, since the amplitude of the feedback current is reduced and the bases need not be driven as far in the negative direction as previously required to cut off the transistor at the end of a pulse. Accordingly, the blocking capacitor will be recharged to the trigger level of the transistor more rapidly, increasing the pulse rate of the circuit. However, the improved linearity of the circuit and the reduction of frequency drift obtained through the use of the isolating network adequately compensates for this problem. It has been found that the use of the described isolating impedance narrows the frequency spectrum, as in FIG. 9, to that which is substantially the minimum sin X/X spectrum that would be obtained by a fixed R.F. frequency pulse modulated generator.

Since the recharging circuit for blocking capacitor 128 includes the resistance of thermistor 192, it will be seen that the value of that resistance will serve to regulate the rate at which the capacitor can recharge after the end of a given pulse, and thus will regulate the repetition rate of oscillations in transistor Q1. It is in this manner that the value of the resistance is translated into a pulse repetition rate.

An additional feature of the circuit of the present invention is the provision of diode 132 which serves to produce a higher effective operating voltage for the d.c. feedback legs of the circuit and thereby further improves the linearity of operation and the stability of the transmitter. The improved stability and linearity of the transmitter circuit will be better understood from a detailed consideration of the operation of the circuit of the present invention as shown in FIG. 8, taken in conjunction with the graphical illustrations of the waveforms appearing in the circuit, as shown in FIGS. 10, 11, and 12.

Initially, with switch 205 open, the transistor Q1 is biased to cut-off. In this condition, the leakage current flow through the transistor is exceedingly small, on the order of ten microamps, or less. This leakage current is smaller than that across the exterior casing of the battery cell, and thus the shelf-life of the transmitter before it is activated is limited only by the shelf-life of the battery.

With the switch open, the voltage at the collector 146 is the battery voltage, in this case 1.6 volts. Capacitor 128 insures that the voltage on the base 144 of Q1 is below the trigger voltage level, which in this case is 0.57 volts, voltage drop across capacitor 128 being 1.6 volts and the bias voltage applied to the base electrode being zero volts.

Upon closure of switch 205, the current begins to flow from the collector electrode, which is a battery potential, through the switch and through diode 132 and the RC network 138 to ground, the high instanteous impedance of the base-emitter junction of Q1 preventing current flow through the thermistor 192 and base 144 to ground. The voltage on the base begins to rise as capacitor 203 charges, and when it reaches the trigger level, transistor Q1 becomes conductive, dropping the collector voltage toward ground potential and causing a current flow from battery 172 through the lower half of coil 18 to the ground potential. The voltage induced in the upper half of coil 18 by this current flow produces a negative going pulse which cuts off the transistor. The pulse excites the tank into oscillation, producing a positive going pulse which is fed back through capacitor 128 to the base of the transistor, turning it back on. This cycle repeats itself, exciting the tank circuit into a resonant oscillation, the amplitude of the oscillation reaching a maximum value after about two complete cycles, and the circuit rapidly reachings it nominal oscillating frequency. This operation is illustrated in FIGS. 10A and 10B, and the enlarged corresponding waveforms of FIGS. 11A and 11B, which illustrate circuit waveforms during a single burst of RF energy.

As seen at waveform 206 in FIG. 10A, which represents the waveform generated in the tank circuit, and thus the waveform appearing on the collector of Q1, each pulse may be divided into three general parts. The initial or rise interval during which the circuit achieves full oscillation after the switch is closed, extends from time $T_0$ to time $T_1$. The maximum energy interval extends from time $T_1$ to time $T_2$ and during this time the amplitude of the oscillations is high, and the transistor is turned on and off during each cycle by the feedback voltage 207 shown in FIG. 10B. At time $T_2$ the average d.c. voltage on the feedback capacitor 128 has gone sufficiently negative, and the amplitude of the oscillations has declined to the point where the positive excursion of the oscillation is insufficient to turn on the transistor. At this point, the oscillations begin to decay exponentially, this decay taking place between times $T_2$ and $T_3$, the oscillation stopping at $T_3$. The initial portions of graphs 206 and 207 of FIGS. 10A and 10B are illustrated in an expanded form in FIG. 11, at graphs 11A and 11B, respectively.

Figure 11A:
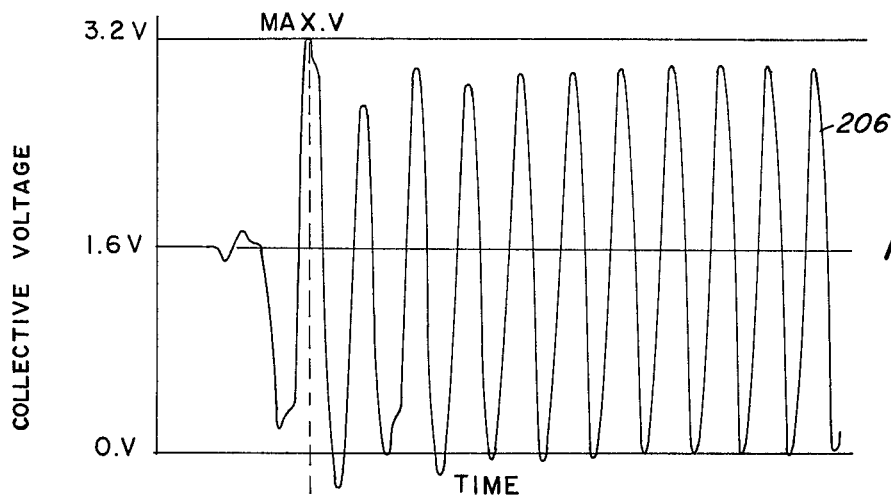
FIGS. 11A and 11B are enlarged illustrations of the waveforms of FIGS. 10A and 10B.
Figure 11B:
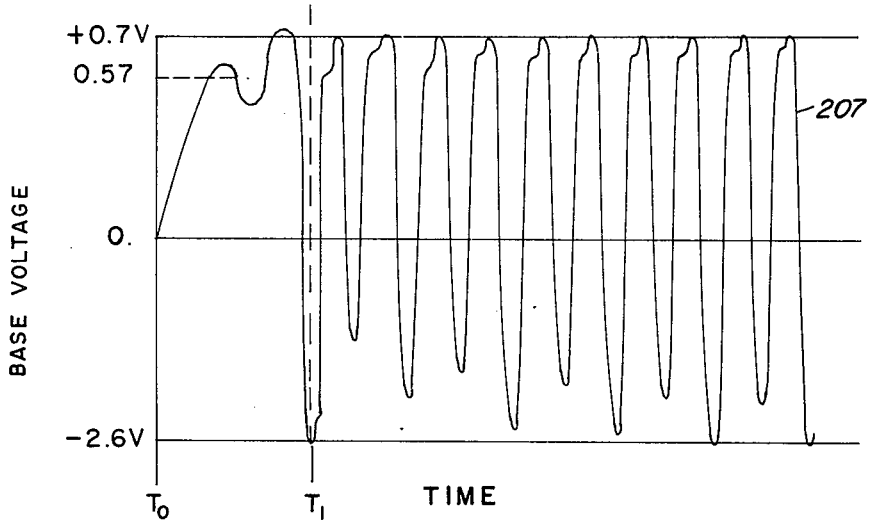
Figure 12:
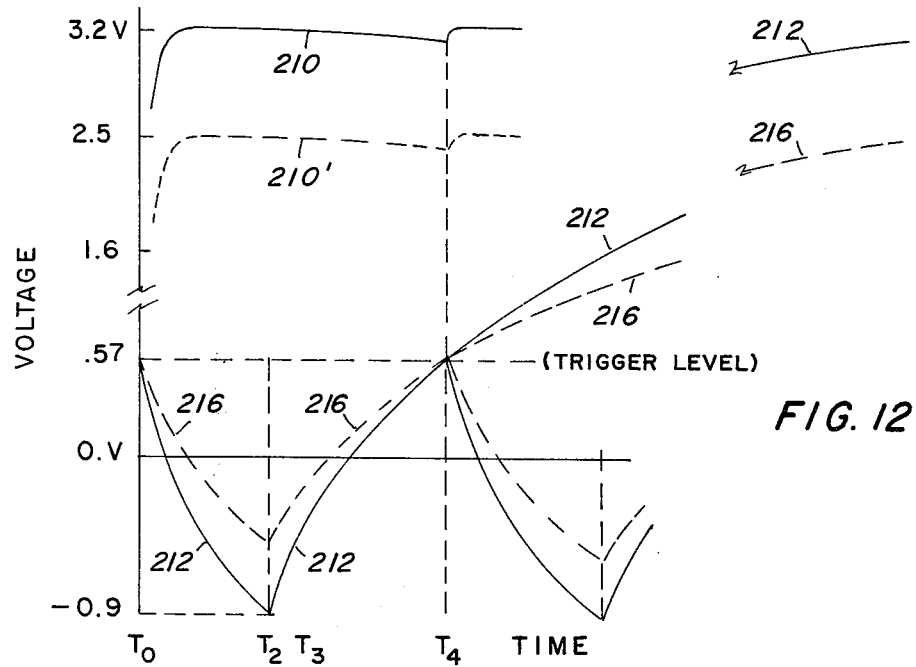
FIG. 12 is a graphical illustration of the control voltage of the transmitter oscillator.

As may be seen in FIGS. 11A and 11B, the closing of switch 205 at time $T_0$ causes the voltage on the base electrode to rise from zero to slightly above the trigger level of 0.57 volts, turning on Q1 and causing the tank circuit to enter resonant oscillation. It will be noted that the collector voltage will oscillate about the battery voltage of 1.6 volts, producing a peak-to-peak amplitude which will depend on the ratio of the turns of winding 18 on either side of the tap 200; in this illustration, the peak-to-peak voltage is 3.2 volts. This voltage is fed back to the base of Q1 from the junction of the tank circuit with capacitor 128, which point is 180° out of phase with the collector, as may be seen in FIGS. 11A and 11B. Since the base of Q1 is driven to the trigger level of 0.57 volts by current supplied through thermistor 192, the positive feedback to the oscillator winding 18 by way of network 202 will be effectively clamped at this positive trigger level (e.g. 0.57 volts), as may be seen in FIGS. 10B and 11B. Therefore, this feedback signal is effectively translated to an approximate average negative value of 0.9 volts at the termination of a burst, this value being the approximate average between plus 0.57 volts and minus 2.6 volts. Thus, a negative voltage appears between the base and emitter of transistor Q1, but is stored on the blocking (or timing) capacitor 128 as long as the peak negative value of the waveform of FIG. 10B does not exceed the maximum reverse base-emitter voltage (4 volts) of Q1. If this base-emitter voltage were to be exceeded three effects would be produced: 1) an unstable charging bias would result, leading to non-reproducible signal bursts; 2) excessive current would be drawn from the battery, and 3) the load compensation network 138 would function improperly. The value of the peak voltage of FIG. 10B is principally a function of the turns ratio and loading of network 198.

For the first few microseconds of the burst, i.e., for the first 20 or 30 cycles of oscillation, the amplitude of the oscillation gradually increases. This is due to the fact that the capacitor 128 is a load on the circuit until it charges to $-0.9$ volts; the load is initially relatively large but gradually decreases as the capacitor asymtotically approaches the $-.9$ volt level. At the same time, however, the supply voltage to the tank circuit decreases, as shown in waveform 208 in FIG. 10D, due to the initial load placed across capacitor 152, and this compensates for the load and holds the amplitude of the oscillations to the desired level, contributing to the stability of the circuit and the resultant narrow RF spectrum.

As capacitor 128 discharges exponentially during the oscillation of the circuit, the length of time during which the transistor Q1 remains conductive for a given cycle gradually diminishes, so tht the frequency of oscillation increases over the width of the pulse. At the same time, since the transistor conducts for a lesser period of time, the amplitude of the oscillations is gradually reduced, as may be seen in FIG. 10A, until a point is reached at which the negative charge on the capacitor becomes so great that the positive voltage swings of the tank circuit cannot bring the base of the transistor to its triggering threshold. This occurs at time $T_2$ in FIG. 10 and signals the start of the decay period of the pulse, in which the oscillations diminish exponentially, as illustrated in FIG. 10A, finally ending at time $T_3$, about 15 microseconds after the initiation of the burst. The remainder of the burst, from $T_3$ to $T_4$, represents the decay of the oscillation, during which time there is insufficient feedback to maintain the oscillations. The total pulse time in the preferred embodiment of the invention is approximately 20 microseconds, with the rise time of the pulse requiring approximately 3 percent of that time and the decay time requiring about 20 percent of the total pulse width, and the circuit produces a very stable, constant-length pulse.

Capacitor 152, which is connected to battery 172, has several functions in this circuit operation. Since the transistor Q1 draws high instantaneous current and since batteries have varying internal impedances, the use of a battery to directly supply the current to the tank would produce an unstable circuit operation and would detract from the reproducibility of the circuit, since each battery would produce a different circuit operation, which would vary with the state of the charge in the battery. The capacitor serves to provide a reproducible source impedance and thereby removes the effect of battery impedance variations from the circuit. Capacitor 152 also provides an increasing supply voltage to the oscillator during the time period $T_2$ to $T_3$. The addition of this positive slope voltage in the base circuit of transistor Q1 aids in controlling the base conduction angle, and thereby improves the frequency stability and pulse width of the oscillator.

During the course of a single burst, the high positive voltage of approximately 3.2 volts appearing on the collector of Q1 is fed through diode 132 to storage capacitor 203, providing at line 139 (FIG. 8) a high voltage source. This voltage across capacitor 203 is indicated by waveform 210 in FIG. 10C, and may be approximately 3v. At the termination of a burst at $T_3$, the high voltage on capacitor 203 starts charging capacitor 128, the charging circuit including the resistance of thermistor 192 When the voltage on capacitor 128 reaches 0.57 volts at time $T_4$ the transistor conducts, initiating another burst of oscillations. The rate at which capacitor 128 charges determines the length of time between the end of one burst at $T_3$ and the start of the next burst at $T_4$; this charging rate is determined by the RC constant of capacitor 203, and thermistor 192. Thus, the temperature of the thermistor determines the burst repetition rate.

The charging and discharging of capacitor 128 is illustrated in FIG. 12 wherein waveform 212 represents the average d.c. voltage across this capacitor and thus the voltage applied to the base of transistor Q1. As shown, during the period $T_1$ through $T_3$, during which period oscillations are being produced by the tank circuit, the average voltage across the capacitor increases in a negative direction from the trigger level of approximately 0.57 volts to a negative value, for example −0.9 volts. At this time, the peak value of the oscillations has decreased to the point that the base of transistor Q1 can no longer be driven to its trigger level, and accordingly it stops switching to its conductive state on each oscillation. The oscillations then die out rapidly, as may be seen in FIG. 10B, bringing the burst to an end at time $T_3$. The capacitor immediately begins charging toward the value of the voltage across capacitor 203, represented by line 210 in FIG. 10C and in FIG. 12, waveform 212 following an exponential curve toward the value of that voltage. The time constant of capacitor 203 and the resistance of thermistor 192 determine the slope of line 212 and thus determine the time period between $T_2$, when the transistor is turned off and $T_4$, when the capacitor 28 reaches the trigger level and turns the transistor back on to initiate another burst.

The foregoing operation of the transmitter circuit is based on the assumption that the transmitter winding 18 has a fixed minimum load on it. However, if the load is changed, as by movement of an object into the vicinity of the coil, energy will be coupled out of the winding, lowering its "Q" and resulting in a lower oscillation amplitude. Such a load may be in the form of small metallic objects, or in the form of some other dielectric material such as human tissue. The consumption of power by such an object in effect introduces a resistance into the resonant circuit, dampening the oscillations and reducing their amplitude. The effect of this is to reduce the maximum voltage applied to diode 134, thereby reducing the maximum voltage built up across capacitor 203, for example to the level indicated by voltage level 210' in FIG. 12. Since there is, under these conditions, a lower maximum value of the alternating current applied to the base of transistor Q1, the average voltage across capacitor 128 will not have to charge to as large a negative voltage to cut the transistor off. Therefore, the average d.c. voltage across the capacitor will follow waveform 216 in FIG. 12 instead of waveform 212.

As shown in FIG. 12, the voltage across capacitor 128 becomes more negative from time $T_1$ to time $T_2$, at which time the transistor is cut off, for example at a voltage of −0.6 volts. The capacitor 128 will then begin to charge toward the lower voltage level 210' following the exponential curve 216. As illustrated in FIG. 12, curve 216 intersects curve 212 at the trigger level voltage of +0.57 volts at time $T_4$, thereby firing transistor Q1 after the same time interval as the transistor is fired under the unloaded condition. Accordingly the pulse rate of the system is substantially unaffected by loading.

Although the exact values and slopes of the curves illustrated in FIG. 12 will vary for different circuit configurations, the principle of operation, in which compensation for variations due to loading of the circuit is provided, will be the same. This compensation is provided by the high voltage circuit which includes diode 132, giving improved stability of the circuit. Furthermore, the fact that capacitor 128 is charging toward a voltage higher than the battery voltage causes the circuit to operate on a more linear portion of the exponential curve, and giving a more accurate burst interval.

Figure 13:
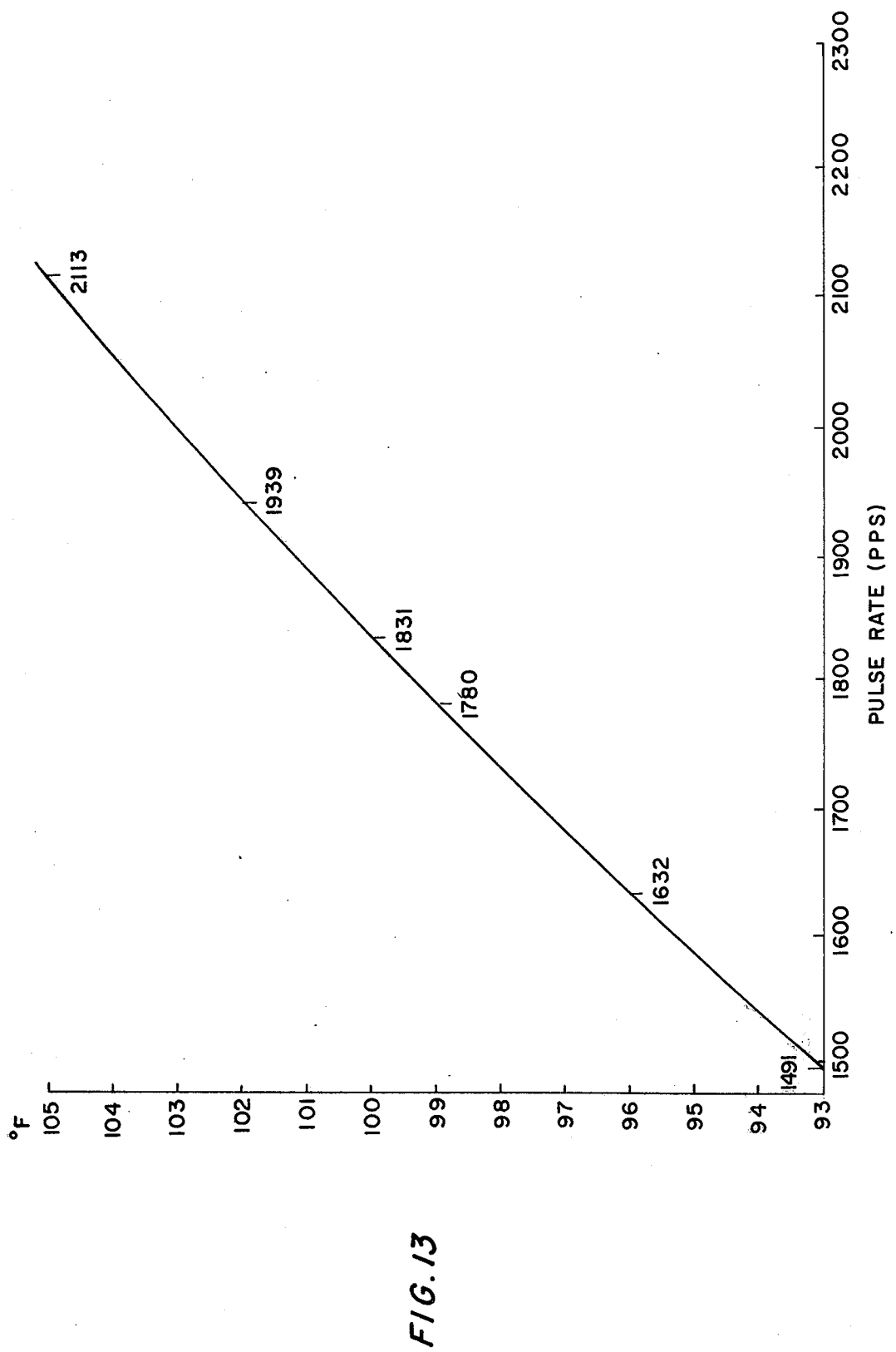
FIG. 13 is a graphical presentation of the temperature vs. frequency response of the transmitter of FIG. 9.

The variation in burst rate in the circuit of the present invention for variations in the temperature to which the thermistor 192 is subjected is shown in FIG. 13. This figure graphically illustrates a typical temperature. versus burst rate characteristic of a sensor-transmitter constructed in accordance with the present invention. The burst rate varies from, for example, 1491 bursts per second at a sensed temperature of 93° F. to 2113 pulses per second at a sensed temperature of 105° F. It has been found that the transmitter cannot produce an exactly linear output over thus temperature range, and this the characteristic curve varies in slope from about 48 bursts per degree at 93°F. to about 54 bursts per degree at 105°F. This variation in slope can produce an inaccuracy in the measured temperature and it is therefore important to select components for the circuit that will produce a characteristic response curve as nearly linear as possible, and to make sure that each transmitter matches a standard curve within about two or three pulses per degree.

Because of the changing slope of the characteristic curve, it is necessary also to carefully design the receiver circuit which is used with the sensor-transmitter of the present application to take this slope into account. Such a receiver is illustrated in copending application Ser. No. 306,253, referenced hereinabove. As has been noted, that application is a Continuation-in-Part of both application Ser. No. 199,675 of Charles H. Fuller, entitled "Physiological Testing System," filed Nov. 17, 1971; and application Ser. No. 299,368 of Carl E. Herring, filed Nov. 19, 1971 and entitled "Measuring and Display System," which applications also disclose a receiver and display system which is capable of accepting signals from the transmitter described herein and producing an accurate display of the measured temperature.

Figure 14:
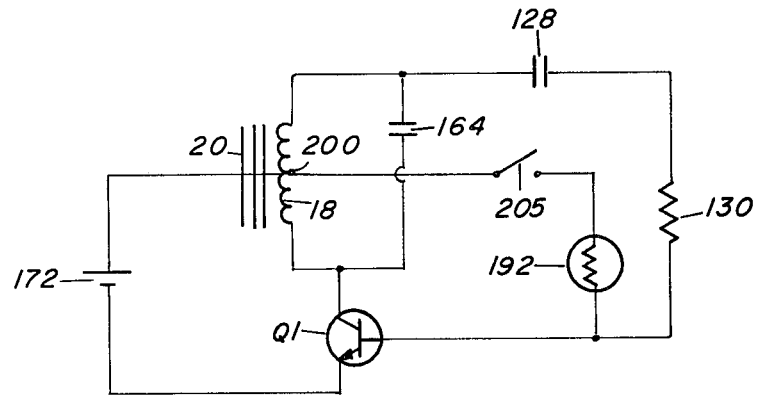
FIG. 14 is a modified form of the transmitter.

A number of variations in the transmitter circuit are possible without departing from the scope of the present invention. For example, another embodiment of the invention is illustrated in FIG. 14, which is similar to that illustrated in FIG. 8, except that the diode 132, the high voltage capacitor 203 and the resistor 204 are omitted and the thermistor 192 is connected between the base of the transistor Q1 and the tap 200 of the coil 18. While this form of the transmitter also transmits a signal that is characterized by a narrow spectrum and generates bursts at a frequency that is a linear function of temperature over the range of interest independently of the load, it is subject somewhat to jitter. In other words, the recurrence intervals betweeen successive bursts of energy are somewhat irregular. Such irregularity is avoided in the circuit of FIG. 8 by virtue of the high voltage source provided by the diode circuit and the storage capacitor 203. The use of a high voltage provides a steeper slope on the recharging waveforms 212 and 216 (FIG. 12), thus enabling the circuit to operate on a more linear portion of the exponential curve. In addition, the fact that the battery output voltage decreases slightly at each burst provides additional assurance that the end of each burst will occur at an exactly predictable time, providing additional stability on a pulse-to-pulse basis. Over a long period variations due to jitter will average out, but where accurate measurements are required over a short period of time, it is essential to reduce the pulse jitter as far as possible. Furthermore, a jitter-free operation under normal circumstances allows use of an imposed jitter as an information carrying signal, if desired.

In other modifications of the circuit, the thermistor may be located elsewhere in the circuit, and more than one thermistor may be employed to provide temperature compensation for the unit.

Figure 15:
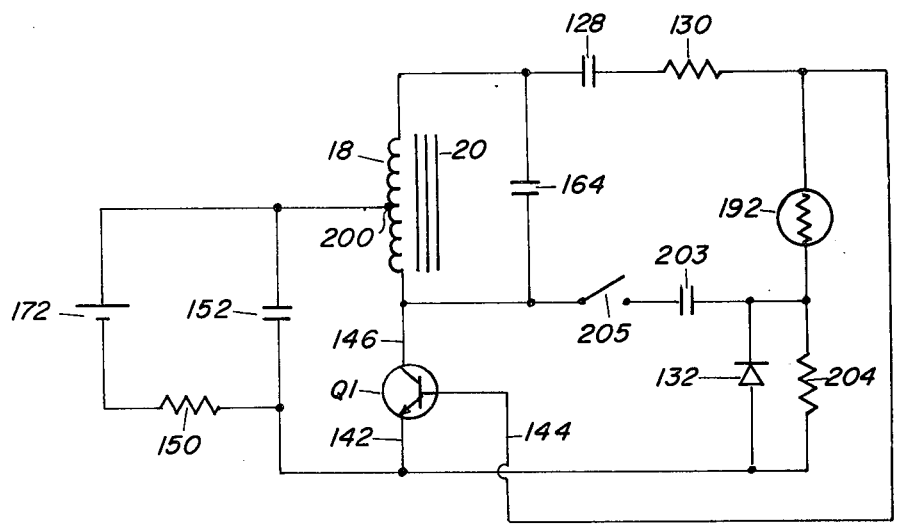
FIG. 15 illustrates another form of the transmitter.

Another embodiment of the invention is illustrated in FIG. 15, wherein the circuit is modified by interchanging the capacitor 203 with the diode 132, the remainder of the circuit being the same. This particular circuit functions similarly to the circuit of FIG. 8 when operating, but possesses the characteristic that it is not self-exciting when switch 205 is closed. With this circuit, excitation is obtained by means of an external transmitter, which transmits energy at the frequency to which the resonant circuit is tuned for a short period of time until the oscillation is self-sustaining.

Although the sensor-transmitter of FIG. 15 is designed to remain operative until the battery supply wears out once the device has been activated by closing the switch cover on the housing, nevertheless it is possible to prolong its life, if desired. This may be accomplished simply by placing the unit on a plate of conductive metal, such as aluminum or copper. The transmitter will then induce eddy currents in the metal, producing such a heavy loading effect on the coil that the oscillator becomes inoperative. When removed from the plate, if the device of this FIG. does not begin to oscillate it can easily be started by exposing it to any R.F. transient. Additional variations of the transmitter circuit will be apparent to those of skill in the art; for example, two transistor oscillator circuits, tank circuits having a portion of the coil in the collector circuit and a portion of the coil in the emitter circuit and the like may be used if desired.

The selection of component values within the present circuit is important and must be done carefully to obtain an output that is as linear as possible for the range of temperatures to which the thermistor will be subjected, and an output that is as reproducable from one circuit to another as possible.

In order to insure the accuracy of the output curve of the subject transmitter, each sensor is calibrated by selecting a thermistor after the remaining circuitry has been assembled. A thermistor is selected that will produce a pulse rate above the desired level at a mid-point temperature; for example, 101°F. The unit is then immersed in an oil bath held at the selected temperature, and a slowly rotating abrasive wheel is brought into contact with the exposed thermistor to grind away a part of the resistive material. This grinding continues until the thermistor produces a pulse rate which represents the nominal temperature, for example, 1831 cycles per second. In this manner the device can be dynamically calibrated to be very accurate. This calibration is made possible by the fact that the thermistor is located on the outside of the housing and is thus accessible.

Since the embodiment disclosed herein is particularly adapted for medical applications, it is directed essentially to a construction that is particularly adapted to restrict the unit to a one-time use, with the switch and battery covers snapping into place on the housing so as not to be easily removeable, thereby preventing deactivation of the device, and preventing battery replacement. Thus, after the sensor transmitter has been activated and used on a patient, it will not normally be used on another patient, but rather will be returned to the manufacturer or other service organization for removal of the switch cover and separation of the switch wires, replacement of the battery, recalibration, and sterilization. The unit may then be returned to the purchaser for further use. The ability to be recycled in this manner produces a considerable savings over prior single-use devices which were thrown away after use, and could not be recycled.

Thus, there has been disclosed a transmitter circuit and housing which is designed to provide quick and accurate assembly, ease of use, a high degree of reproducability, and accurate transmission of a measured temperature. The transmitter is designed to produce a very narrow frequency spectrum, a steady pulse rate accurately representing the measured temperature, and a stable, substantially linear operation. The transmitter is mounted in a housing which is tough, yet economical and comfortable to wear, which produces a fast response to measured temperature while eliminating the effect of ambient temperature changes, producing an ideal telemetering system for transferring information concerning physiological conditions to a remote receiver. Although particular embodiments of the invention have been described and illustrated, it will be apparent to those of skill in the art that various modifications may be made without departing from the true spirit and scope of the invention as described in the following claims.

What is claimed is:

1. In a blocking oscillator for generating a sequence of bursts of oscillations, said blocking oscillator having an amplifying device that has a control element,
    a resonant circuit including an inductor and a tuning capacitor operatively connected to said amplifying device, said oscillator also including a blocking capacitor connected to said resonant circuit for developing a control bias;
    means for applying said control bias to said control element to quench said oscillations when the bias attains one value and to initiate said oscillations when said bias attains another value, said control capacitor charging in one direction while said oscillator is oscillating and in the other direction when said oscillator is quiescent to change said bias;
    an isolation impedence connecting said blocking capacitor between said resonant circuit and said control element, whereby intermittent switching of the amplifying element on and off precludes intermittent direct connection and disconnection of said blocking capacitor across said resonant circuit, thereby concentrating the oscillations to a narrow band of frequencies determined by said tuning capacitor and said inductor substantially independently of said blocking capacitor.

2. A blocking oscillator as defined in claim 1 wherein said isolation impedence element is a resistor.

3. In a blocking oscillator for generating a sequence of bursts of oscillations of radio frequency, including an amplifying device in the form of a solid-state element having a control electrode and an output electrode, the oscillator having a tuned circuit including an inductor and a tuning capacitor operatively connected to said electrodes, the improvement comprising:
    a bias control circuit for said oscillator including an isolating resistor and a blocking capacitor connected between said tuned circuit for said control electrode for developing a control bias in accordance with the oscillations in said tuned circuit, wherein the bias on said control electrode charges in one direction while said oscillator is oscillating, finally attaining a bias which quenches said oscillations, and charges in the other direction when said oscillator is quiescent, to reach a value at which oscillations are initiated; and high voltage means connected between said output electrode and said control electrode for stabilizing the time between successive ones of said bursts.

4. The blocking oscillator as defined in claim 3, wherein said high voltage means comprises a rectifying element and storage capacitor, the junction between said capacitor and said rectifying element being connected to said control electrode.

5. The blocking oscillator as defined in claim 3, further including temperature senstive variable impedence means connected between said high voltage means and said blocking capacitor to control the rate of charging of said blocking capacitor while said oscillator is quiescent, whereby the time between successive ones of said bursts is varied in accordance with the temperature sensed by said variable impedence.

6. In a blocking oscillator for generating a sequence of bursts of oscillations of radio frequency at a burst rate that corresponds to the value of a physiological parameter of a subject, said oscillator having an amplifying device in the form of a solid-state element having a control electrode and an output electrode and a tuned circuit including an inductor and a tuning capacitor operatively connected to said electrodes, said oscillator including a sensing element having a resistance that varies in accordance with the value of said parameter, the improvement comprising:
 a storage capacitor connected to said tuned circuit for developing a control bias in accordance with the strength and duration of oscillations in said tuned circuit; and
 a bias control circuit including said sensing element and a resistor connected to said control electrode and to said blocking capacitor whereby said control capacitor changes the bias on said control electrode in one direction while said oscillator is oscillating, finally reaching a bias which quenches said oscillations, and in the other direction when said oscillator is quiescent, to reach a value at which oscillations are initiated, the rate of change of bias while said oscillation is quiescent varying in accordance with the value of said sensing element.

7. The blocking oscillator of claim 6, further including means for compensating for variations in the loading of said tuned circuit, said compensating means comprising a source of high voltage connected to said blocking capacitor for maintaining constant the time between successive ones of said bursts.

8. The blocking oscillator of claim 7, further including means for maintaining a narrow spectrum of frequencies during each of said bursts of radio frequency, said last named means comprising an isolating impedance connected to said blocking capacitor.

9. The blocking oscillator of claim 8, further including power supply means for said amplifying device, said power supply means including a battery and a capacitor connected to each other and to said output electrode.

10. The blocking oscillator of claim 9, wherein said power supply means is connected to said output electrode through at least a part of said inductor.

11. The blocking oscillator of claim 9, wherein said source of high voltage comprises a storage capacitor connected to said blocking capacitor through said sensing element.

12. The blocking oscillator of claim 11, wherein said source of high voltage further includes rectifying means connected between said tuned circuit and said storage capacitor.

13. The blocking oscillator of claim 12, wherein said sensing element comprises a thermistor adapted to monitor the temperature of a subject, and wherein said inductor serves as an antenna to transmit said bursts of radio frequency oscillations.

14. The blocking oscillator of claim 13, further including housing means for receiving each element of said oscillator, said housing being dimensionally rigid to protect said elements, and means for securing said housing to said subject whereby said thermistor is brought into thermal equilibrium with said subject.

15. The blocking oscillator of claim 14, wherein said housing has receptacle means for receiving said thermistor and holding it against the surface of said subject when said housing is secured to the subject, and further including thermal insulation means between said thermistor and said housing to thermally isolate said thermistor from said housing, whereby said thermal equilibrium is achieved.

16. The blocking oscillator of claim 15, further including thermally insulating cover means for said housing, whereby said sensing element and said oscillator are thermally isolated from sudden changes in ambient temperature, but remain sensitive to changes in the temperature of said subject.

17. In a physiological testing unit to be secured to a subject:
 a blocking oscillator for generating a sequence of bursts of oscillations at a burst rate that corresponds to the value of a physiological panameter of the subject, said oscillator having an amplifying device including a control electrode and an output electrode and having a resonant circuit operatively connected to said electrodes, said resonant circuit including an antenna winding adapted to emit signals corresponding to said oscillations;
 a blocking capacitor connected to said resonant circuit for developing a control bias;
 a bias control circuit including a sensing element responsive to said parameter connected to said control electrode and to said blocking capacitor, said bias control circuit changing the bias on said control electrode in one direction while said oscillator is oscillating, finally reaching a bias level which quenches said oscillations, and changes the bias level on said control electrode in the other direction when said oscillator is quiescent, finally reaching a bias level at which oscillations are initiated, the rate of change of bias level while said oscillator is quiescent varying in accordance with the value of the parameter detected by said sensing element whereby said burst rate varies with the value of said parameter;
 a housing enclosing said oscillator;
 means mounting said sensing element exteriorly of said housing; and
 means for externally removably attaching said unit to the subject, said sensing element being mounted on the housing to detect a desired physiological parameter of the subject and being connected to said oscillator bias control circuit to modulate said signals in accordance with such parameter.

18. A physiological testing unit as defined in claim 17, wherein said resonant circuit is electrostatically shielded in order to reduce electrostatic radiation to and from the transmitter without substantially reducing the magnetic inductive transmission.

19. A physiological testing unit as defined in claim 17, wherein said winding encircles a powdered iron core.

20. A physiological testing unit as defined in claim 19, wherein said oscillator is powered by a battery of cylindrical configuration and wherein said iron core is in the form of a tubular cylinder that encircles said battery.

21. A physiological testing unit as defined in claim 17, wherein said sensing element comprises a thermistor which is to be placed in close proximity to the skin of the subject to detect the temperature of the subject.

22. A physiological testing unit as defined in claim 17, wherein said means for securing said assembly to the subject comprises a thin, double-faced adhesive member.

23. A physiological testing unit as defined in claim 17, wherein said housing comprises a rigid case member formed with a plurality of shaped interior cavities, an exterior switch receptacle, and an exterior receptacle for said sensing element; said resonant circuit, said winding, said core, and said battery all being mounted in corresponding cavities within said case member for accurate placement;

a flexible cover member secured over said rigid case member; and an adhesive member having an aperture, one side of said adhesive member being secured to the bottom of said flexible cover member and to the bottom of said case, the other side of said adhesive member being adapted to be secured to the subject said sensing element protruding through said aperture of said adhesive member and being adapted to contact the subject when the unit is in place on the subject.

24. A physiological testing unit as defined in claim 23, wherein said sensing element is a thermistor mounted in said exterior sensing element receptacle by means of a thermally insulating adhesive.

25. A small, self-contained physiological testing unit to be externally secured to a patient and adapted to transmit signals corresponding to the temperature of the patient, comprising:

a thermistor adapted to be placed adjacent the surface of the patient's skin to detect its temperature, said thermistor having a pair of electrodes;

an oscillator circuit having an antenna winding, said oscillator being controlled by the thermistor to inductively transmit signals modulated in accordance with the detected temperature;

a tubular iron core composed of powdered iron particles held together with an electrically insulating, non-magnetic binder, said winding being wound on the outside of said core;

a power supply for said oscillator circuit including a battery fitting snugly within said core;

a dimensionally rigid case member formed with a plurality of internal cavities, each cavity being formed to receive a corresponding one of said core and of said electrical components making up said oscillator circuit, said cavities locating said components in such a way that substantially all electrical connections for said oscillator circuit may be made by means of the lead wires on said components;

means for mounting said thermistor on the exterior of said case member, said thermistor electrodes being connected through said case member to said oscillator circuit;

battery cover means for securing said battery within said case member;

a flexible, flanged cover secured to said rigid case member and together with said case providing thermal insulation for said electrical components, said cover providing a pliant outer cover for the testing unit; and a thin adhesive member having adhesive on both sides, one side of the adhesive member being secured to the bottom of the flanged cover and to said case member, said unit being adapted to be secured externally to the patient by the adhesive member with said thermistor adjacent the patient's skin.

26. The testing unit of claim 25, wherein said means for mounting said thermistor comprises a first external receptacle on said case member, and a heat insulating adhesive securing said thermistor to said receptacle.

27. The testing unit of claim 26, wherein at least one surface of said thermistor is exposed for contact with said patient's skin, said exposed surface being available for calibration of said unit after assembly thereof.

28. The testing unit of claim 26, further including a pair of helical coils interconnecting said thermistor electrodes and said oscillator circuit, said helical coils being bifilar to reduce the effect of said transmitted signals on said oscillator and being of thin wire to thermally isolate said thermistor from said case member and said oscillator circuit.

29. The testing unit of claim 26, further including a second external receptacle on said case member, said second receptacle receiving electrical component lead wires for said oscillator circuit from within said case, said lead wires being separated to form an open switch to prevent operation of said oscillator; and switch cover means adapted to engage said second receptacle and to close said switch, whereby said oscillator is activated.

30. The testing unit of claim 29, wherein said switch cover means includes means for securing said cover to said case member to prevent reopening of said switch.

31. The testing unit of claim 30, wherein said battery cover means includes flange means for preventing easy removal of said battery, said switch cover and said battery cover insuring single use of said testing unit, while permitting recycling through replacement of the battery said recalibration of said unit.

32. The testing unit of claim 25, wherein said lead lines of said electrical components are interconnected by means of an electrically conductive epoxy adhesive which cures at room temperature, whereby said electrical circuit is assembled without the application of heat.

33. The testing unit of claim 25, wherein said oscillator is a blocking oscillator for generating recurring bursts of oscillations at radio frequency, said oscillator including an amplifying device in the form of a transistor having collector and base electrodes, and a tuned circuit comprising said antenna winding and a tuning capacitor connected between said collector and base electrodes.

34. The testing unit of claim 33, wherein said oscillator further includes a bias control circuit comprising an isolating network having an isolating impedance and a blocking capacitor, said isolating network being connected between said tuned circuit and said base electrode, and high voltage means connected to said isolating network for stabilizing the time between successive bursts.

35. The testing unit of claim 34, wherein said thermistor is connected between said high voltage means and said isolating network, and between said high voltage means and said base electrode, whereby the resistance of said thermistor regulates the repetition rate of said bursts.

36. The testing unit of claim 35, wherein said high voltage means comprises rectifying means and a storage capacitor connected between said collector electrode and said thermistor.

37. For an oscillator of a radio frequency transmitter, a winding wound on a tubular magnetic core that encircles a miniature battery, said core being composed of carbonyl iron.

38. A device as defined in claim 37, wherein said core is grooved, and then etched to restore its insulative characteristics, said grooves receiving the turns of said winding.

39. A device as defined in claim 38, further including an electrostatic shield encircling said winding and covering at least one end of the winding and core assembly.

40. The physiological testing unit of claim 17, wherein said sensing element comprises means responsive to changes in the temperature of the subject.

41. The testing unit of claim 40, further including means for compensating for variations in the loading of said resonant circuit, said compensating means comprising a source of high voltage connected to said blocking capacitor for maintaining constant the time between successive ones of said bursts.

42. The testing unit of claim 41, further including means for maintaining a narrow spectrum of frequencies during each of said bursts of oscillations, said last named means comprising an isolating impedance connected to said blocking capacitor.

43. The testing unit of claim 42, further including power supply means for said oscillator, said power supply having a battery and a capacitor connected to each other and to said output electrode.

44. The testing unit of claim 43, wherein said power supply means is connected to said output electrode through at least a part of said antenna winding.

45. The testing unit of claim 41, wherein said source of high voltage comprises a storage capacitor connected to said blocking capacitor through said sensing element.

46. The testing unit of claim 45, wherein said source of high voltage further includes rectifying means connected between said tuned circuit and said storage capacitor.

47. The testing unit of claim 40, wherein said housing has receptacle means for receiving said sensing element and holding it against the surface of a subject when said housing is secured to the subject, and further including thermal insulation means between said sensing element and said housing to thermally isolate said sensing element from said housing, whereby said sensing element can attain thermal equilibrium with the subject.

48. The testing unit of claim 47, wherein said housing includes means to thermally isolate said sensing element and said oscillator from sudden changes in ambient temperature, said sensing element remaining sensitive to changes in the temperature of said subject.

49. In a physiological testing unit to be secured to a subject:
a blocking oscillator including an amplifying device having a control element for generating a sequence of bursts of oscillations, said oscillator including a resonant circuit operatively connected to said amplifying device and including an antenna winding and a tuning capacitor adapted to emit signals corresponding to the detected physiological condition;
a blocking capacitor connected to said resonant circuit for developing a control bias;
means for applying said control bias to said control element to quench said oscillations when said bias attains one value and to initiate said oscillations when said bias attains another value, said blocking capacitor charging in one direction while said oscillator is oscillating and in the other direction when said oscillator is quiescent to change said bias;
an isolation impedance connecting said blocking capacitor between said resonant circuit and said control element whereby intermittent switching of the amplifying device on and off precludes intermittent direct connection and disconnection of said blocking capacitor across said resonant circuit, thereby concentrating the oscillations to a narrow band of frequencies determined by said tuning capacitor and said antenna winding substantially independently of said blocking capacitor;
a housing enclosing said oscillator circuit;
means for externally removably attaching said unit to the subject; and
a sensing element mounted on the housing to detect a desired physiological parameter of the subject and connected to said oscillator to modulate said emitted signals in accordance with such parameter.

50. A physiological testing unit as defined in claim 49 wherein said isolation impedance element is a resistor.

51. The testing unit of claim 49, wherein said housing includes a plurality of shaped interior cavities adapted to receive said oscillator circuit and an exterior sensing element receptacle;
a cover member securable on said housing for protecting and thermally insulating said circuit means;
means for securing said sensing element in said exterior sensing element receptacle; and
means for securing said housing to said subject so that said sensing element is capable of sensing said physiological parameter.

52. The unit of claim 51, wherein said sensing element comprises a thermistor.

53. The unit of claim 51, wherein said cover member is flexible and provides a pliant outer covering for the testing unit.

54. The unit of claim 51 wherein said means for securing said sensing element includes means for exposing at least a portion of said sensing element for contact with said subject.

55. The unit of claim 51, further including a switch receptacle on said housing, said switch receptacle receiving electrical circuit lead wires from within said housing, said lead wires forming an open switch to prevent operation of said electrical circuit; and
switch closure means adapted to engage said switch receptacle to close said open switch and permit operation of said electrical circuit.

56. The unit of claim 55, further including means on said switch closure means for preventing reopening of said switch, whereby said electrical circuit remains in operation once activated.

57. A physiological testing unit including a transmitter having a blocking oscillator for generating a sequence of bursts or oscillations of radio frequency and including an amplifying device in the form of a solid-state element having a control electrode and an output electrode, the oscillator having a tuned circuit including a transmitter antenna and a tuning capacitor operatively connected to said electrodes;

a bias control circuit for said oscillator including an isolating resistor and a blocking capacitor connected between said tuned circuit for said control electrode for developing a control bias in accordance with the oscillations in said tuned circuit, wherein the bias on said control electrode charges in one direction while said oscillator is oscillating, finally attaining a bias which quenches said oscillations, and charges in the other direction when said oscillator is quiescent, to reach a value at which oscillations are initiated;

high voltage means connected between said output electrode and said control electrode for stabilizing the time between successive ones of said bursts;

variable impedance means connected between said high voltage means and said blocking capacitor to control the rate of charging of said blocking capacitor while said oscillator is quiescent, whereby the time between successive ones of said bursts is varied in accordance with a parameter sensed by said variable impedance;

a housing enclosing said blocking oscillator, bias control circuit and high voltage means;

means for mounting said impedance means on the exterior of said housing; and means for securing said housing externally on a subject whose temperature is to be sensed with said impedance means in contact with said subject, whereby said testing unit transmits bursts of oscillations having a time rate which corresponds to the temperature being sensed.

* * * * *

UNITED STATES PATENT AND TRADEMARK OFFICE
CERTIFICATE OF CORRECTION

PATENT NO. : 3,949,388
DATED : April 6, 1976
INVENTOR(S) : Charles H. Fuller

It is certified that error appears in the above-identified patent and that said Letters Patent are hereby corrected as shown below:

In the Claims

Claim 6, line 12 (column 21, line 28)
            "storage" should read --blocking--.

Claim 9, line 4 (column 21, line 57)
            after "connected" insert --in parallel--.

Claim 31, line 6 (column 24, line 47)
            "said" first occurrence, should read
            --and--.

Signed and Sealed this

Third Day of August 1976

[SEAL]

Attest:

RUTH C. MASON
*Attesting Officer*

C. MARSHALL DANN
*Commissioner of Patents and Trademarks*